United States Patent
Höpfl

(10) Patent No.: US 6,478,749 B1
(45) Date of Patent: Nov. 12, 2002

(54) DIAGNOSTIC KIT FOR SKIN TESTS, AND METHOD

(75) Inventor: Reinhard Höpfl, Innsbruch (AT)

(73) Assignee: Medigene Aktiengesellschaft Gesellschaft fur Molekularbiologische Kardiologie und Onkologie (DE)

( * ) Notice: Subject to any disclaimer, the term of this patent is extended or adjusted under 35 U.S.C. 154(b) by 0 days.

(21) Appl. No.: 09/486,394

(22) PCT Filed: Jul. 30, 1998

(86) PCT No.: PCT/EP98/04773

§ 371 (c)(1),
(2), (4) Date: Jun. 20, 2000

(87) PCT Pub. No.: WO99/10744

PCT Pub. Date: Mar. 4, 1999

(30) Foreign Application Priority Data

Aug. 27, 1997 (DE) .......................... 197 37 409

(51) Int. Cl.⁷ ................................ A61B 5/00
(52) U.S. Cl. ...................... 600/556; 206/569
(58) Field of Search ............... 600/573, 584; 206/563

(56) References Cited

FOREIGN PATENT DOCUMENTS

| DE | 91 06 105 | 7/1991 |
|---|---|---|
| DE | 91 06 105.9 | 11/1991 |
| EP | 0 386 734 | 9/1990 |
| EP | 0 451 550 | 9/1991 |

OTHER PUBLICATIONS

Viscidi et al., Int J. Cancer, Serologic Response in HPV–Associated Invasive Cervical Cancer, 55(5):780–4, Nov. 11, 1993.*

Park et al., HPV–16–related proteins as the serologic markers in cervical neoplasia, Gynecol Oncol 1998, Apr.; 69(1):47–55.*

Medline, Washington, D.C., USA; Abstract No. 91073133, see abstract, XP002090517 & M. Muller et al, "Identification of seroreactive regions of the human papillomavirus type 16 protein E4, E6, E7 and L1" Journal of General Virology, Bd. 171, 1990, Seiten 2709–2717, Oxford UK.

K. Seedorf, T. Oltersdorf, G. Krämmer and W. Röwekamp, Identification of Early Proteins of the Human Papilloma Viruses Type 16 (HPV 16) and Type 18 (HPV 18) in Cervical Carcinoma Cells, The EMBO Journal vol. 6 No. 1 pp. 139–144, 1987.

Oltersdorf T., K. Seedorf, W. Rowekamp and L. Gissman, Identification of Human Papillomavirus Type 16 E7 Protein by Monoclonal Antibodies, Journal of General Virology 68(Pt 11) pp. 2933–2938, Nov. 1987 (Abstract Only).

Pamela Hawley–Nelson, Karen H. Vousden, Nancy L. Hubbert, Douglas R. Lowy and John T. Schiller, HPV16 E6 and E7 proteins cooperate to immortalize Human Foreskin Keratinocytes, The EMBO Journal vol. 8 No. 12 pp. 3905–3910, 1989.

Ingrid Jochmus–Kudielka, Achim Schneider, Rüdiger Braun, Rainer Kimmig, Ursula Koldovsky, Karl Eduard Schneweis, Klaus Seedorf, Lutz Gissmann, Antibodies Against the Human Papillomavirus Type 16 Early Proteins in Human Sera: Correlation of Anti–E7 Reactivity With Cervical Cancer, Journal of the National Cancer Institute, Aug. 31, 1989.

Martin Müller, Heinrich Gausepohl, Guy de Martynoff, Rainer Frank, Robert Brasseur and Lutz Gissman, Identification of Seroreactive Regions of the Human Papillomavirus Type 16 Proteins E4, E6, E7 and L1, The Journal of General Virology (1990), 71, 2709–2717.

R. Höpfl, M. Sandbichler, N. Sepp, K. Heim, E. Müller–Holzner, B. Wartusch, O. Dapunt, I. Jochmus–Kudielka, J. Ter Meulen, L. Gissmann, P. Fritsch, Skin Test for HPV Type 16 Proteins in Cervical Intraepithelial Neoplasia, The Lancet, vol. 337, p. 373, Feb. 9, 1991.

Cornelia S. McLean, Jane S. Sterling, Justine Mowat, Anthony A. Nash and Margaret A. Stanley, Delayed–type Hypersensitivity Response to the Human Papillomavirus Type 16 E7 Protein in a Mouse Model, Journal of General Virology (1993), 74, pp. 239–245.

Reinhard M. Höpfl, Neil D. Christensen, Michael G. Angell and John W. Kreider, Skin Test to Assess Immunity Against Cottontail Rabbit Papillomavirus Antigens in Rabbits with Progessing Papillomas or After Papilloma Regression, The Society for Investigative Dermatology, Inc., 1993, pp.227–231.

Neil D. Christensen, Reinhard Höpfl, Susan L. DiAngelo, Nancy M. Cladel, Susan D. Patrick, Patricia A. Welsh, Lynn R. Budgeon, Cynthia A. Reed and John W. Kreider, Assembled Baculovirus–Expressed Human Papillomavirus Type 11 L1 Capsid Protein Virus Like Particles are Recognized by Neutralizing Monoclonal Antibodies and Induce High Titres of Neutralizing Antibodies, Journal of General Virology (1994), 75, pp. 2271–2276.

Thesis submitted for the certificated of habilitation of Dr. Höpfl.

* cited by examiner

Primary Examiner—John P. Lacyk
Assistant Examiner—Pamela Wingood
(74) Attorney, Agent, or Firm—Burns, Doane, Swecker & Mathis, LLP

(57) ABSTRACT

A skin test for detecting the immune status with respect to the transforming virus proteins E6 and E7 of human papilloma viruses is provided. The skin test comprises a diagnosis kit containing an effective amount of the protein E6 and/or E7 or at least an immunologically effective portion of E6 and/or E7. The skin test is carried out by intracutaneously applying the protein E6/E7 of the diagnosis kit and visually inspecting the respective skin region to detect reddening.

23 Claims, No Drawings

SEQUENCE LISTING

<160> NUMBER OF SEQ ID NOS: 6

<210> SEQ ID NO 1
<211> LENGTH: 30
<212> TYPE: PRT
<213> ORGANISM: Human papillomavirus type 16
<220> FEATURE:
<221> NAME/KEY: PEPTIDE
<222> LOCATION: (1)..(30)
<223> OTHER INFORMATION: E7 peptide.

<400> SEQUENCE: 1

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp
            20                  25                  30
```

<210> SEQ ID NO 2
<211> LENGTH: 30
<212> TYPE: PRT
<213> ORGANISM: Human papillomavirus type 16
<220> FEATURE:
<221> NAME/KEY: PEPTIDE
<222> LOCATION: (1)..(30)
<223> OTHER INFORMATION: E7 peptide.

<400> SEQUENCE: 2

```
Asp Leu Tyr Cys Tyr Glu Gln Leu Asn Asp Ser Ser Glu Glu Glu Asp
1               5                   10                  15

Glu Ile Asp Gly Pro Ala Gly Gln Ala Glu Pro Asp Arg Ala
            20                  25                  30
```

<210> SEQ ID NO 3
<211> LENGTH: 30
<212> TYPE: PRT
<213> ORGANISM: Human papillomavirus type 16
<220> FEATURE:
<221> NAME/KEY: PEPTIDE
<222> LOCATION: (1)..(30)
<223> OTHER INFORMATION: E7 peptide.

<400> SEQUENCE: 3

```
Pro Ala Gly Gln Ala Glu Pro Asp Arg Ala His Tyr Asn Ile Val Thr
1               5                   10                  15

Phe Cys Cys Lys Cys Asp Ser Thr Leu Arg Leu Cys Val Gln
            20                  25                  30
```

<210> SEQ ID NO 4
<211> LENGTH: 30
<212> TYPE: PRT
<213> ORGANISM: Human papillomavirus type 16
<220> FEATURE:
<221> NAME/KEY: PEPTIDE
<222> LOCATION: (1)..(30)
<223> OTHER INFORMATION: E7 peptide.

<400> SEQUENCE: 4

```
Cys Asp Ser Thr Leu Arg Leu Cys Val Gln Ser Thr His Val Asp Ile
1               5                   10                  15
```

```
Arg Thr Leu Glu Asp Leu Leu Met Gly Thr Leu Gly Ile Val
            20                  25                  30

<210> SEQ ID NO 5
<211> LENGTH: 28
<212> TYPE: PRT
<213> ORGANISM: Human papillomavirus type 16
<220> FEATURE:
<221> NAME/KEY: PEPTIDE
<222> LOCATION: (1)..(28)
<223> OTHER INFORMATION: E7 peptide.

<400> SEQUENCE: 5

Ser Thr His Val Asp Ile Arg Thr Leu Glu Asp Leu Leu Met Gly Thr
1               5                   10                  15

Leu Gly Ile Val Cys Pro Ile Cys Ser Gln Lys Pro
            20                  25

<210> SEQ ID NO 6
<211> LENGTH: 30
<212> TYPE: PRT
<213> ORGANISM: Human papillomavirus type 16
<220> FEATURE:
<221> NAME/KEY: PEPTIDE
<222> LOCATION: (1)..(30)
<223> OTHER INFORMATION: Control peptide.

<400> SEQUENCE: 6

Ser Glu Asn Lys Glu Leu Lys Lys Ala Ile Asp Gly Leu Gln Gly Leu
1               5                   10                  15

Leu Leu Gly Leu Arg Gln Arg Ile Glu Thr Leu Glu Gly Lys
            20                  25                  30
```

DIAGNOSTIC KIT FOR SKIN TESTS, AND METHOD

BACKGROUND OF THE INVENTION

1. Field of the Invention

The present invention concerns a skin test for determining the immune status against human papilloma viruses.

2. Description of the Related Art

Human papilloma viruses (HPV) are closely connected with malignant carcinomas of the anogenital tract, especially the neck of the uterus, the vulva, the penis and the anal duct. "High-risk" HPV types such as HPV 16 transform keratinocytes by means of the viral oncoproteins E6 and E7 contained therein by inactivating tumor suppressor proteins. It is assumed that the two oncoproteins E6 and E7 cooperatively contribute to the immortalizing (Hawley-Nelson, EMBO J., 8, 3905 (1989)).

The cancer cells transformed by HPV express the viral proteins E6 and E7 even in advanced tumor stages. It is assumed that a spontaneous or vaccination-induced immune reaction against these proteins could result in a regression of tumors caused by HPV. Until now, patients showing a spontaneous regression of their disease have not been examined due to the fact that examinations of the cellular defensive reaction in vitro are extremely time-consuming and, nevertheless, show a relatively low sensitivity. The role of the cellular immunological response in the case of vaccinations against HPV associated lesions is unclear.

Skin tests are partly already used in the clinical field in allergiology and for infectious diseases (mainly for clarifying tuberculosis in the form of the known TINE test).

There was, however, practically no specific application for virological questions or for cancer research until now.

Skin tests are also an excellent means for scientific questions and suitable for rapidly and practicably detecting complex cellular immune reactions in vivo. A skin test for examining the cellular immune reaction against "high risk" HPV is already known in prior art. This first application of the skin test for determining an immune reaction against a cancer associated virus was carried out with the coat protein L1 of the "high risk" HPV type 16 (utility model G9106105.9) and thereafter applied in animal models.

There is also a model for the skin test for the mouse; the immune reaction to a transplanted antigen was tested in this case (Mc Lean et al., J. Gen. Virol. 74, 239–245 (1993)).

This known skin test did not detect the humoral immunological response to an HPV infection. In contrast to the cellular defense, the detection of the humoral immune reaction can be carried out relatively easily in the laboratory by means of serological tests. It is considered to be proven that antibodies against three-dimensionally intact structures of the virus coat proteins can neutralize papilloma viruses (Christensen et al. J Gen Virol 75, 2271 (1994)). Antibodies against the early proteins E6 and E7 are associated with malignant tumors of the neck of the uterus (Jochmus-Kudielka et al. J. Natl. Cancer Inst. 81, 1698 (1989)).

A prophylactic vaccination with "virus like particles" consisting of coat proteins would preventively reduce an HPV infection and the risk of cancer associated therewith. The humoral immunological response against HPV, however, does not play a role with respect to the regression of already existing lesions. The serology has therefore an epidemiological significance.

In summary, the experiments with animal models and female patients show that cellular immune reactions against viral proteins are detectable by skin tests. As a result of the data, it can be assumed that an immune reaction against the coat protein L1 is not associated with regression, as in advanced lesions intact virus particles cannot be formed any more. Thus, the transforming virus proteins E6 and E7 are the probable goal of a "healing" immune reaction. These tumor antigens are thus potential candidates for the development of a vaccine if, in addition to the prophylactic effectiveness, a ctherapeutic effectiveness is to be achieved by virus coat proteins. It is assumed that such a vaccination causes an activation of cytotoxic T cells and T helper cells against persistently infected genital lesions.

However, an in vivo test for detecting the success of such a vaccination against E6 and/or E7 by means of the cellular defensive reaction of the immunological system as a reaction to the vaccination has not been known until now.

SUMMARY OF THE INVENTION

Therefore, the object to be solved by the invention is to provide a test by means of which the immune status against E6 and/or E7 proteins of papilloma viruses can easily be detected in vivo. According to the invention, this object is solved by providing the diagnosis kit for skin tests according to independent claim 1 and the process for carrying out a skin test according to independent claim 10. Further advantageous embodiments and aspects of the invention are evident from the dependent claims and the description.

The skin test according to the invention can also be used for detecting spontaneous regressions of papilloma virus carcinoma precursors (CIN).

In a further aspect, the skin test according to the invention can also be used in the field of research in order to examine mechanisms in the regression of lesions caused by HPV.

DETAILED DESCRIPTION OF THE INVENTION

In the following, the present invention is explained by means of an example, wherein the suitability of the skin test in principle for examining vaccination successes is shown with female patients who have not been vaccinated but partly showed spontaneous regressions of the cervix carcinomas and precursors thereof and thus a characteristic which is equivalent to the vaccination success. Synthetic peptides were used for the skin test against HPV16-E6 or -E7. Compared to the use of native proteins or fusion proteins, they have the advantage that a contamination with DNA could be excluded because it is absolutely certain that synthetic peptides are free from any problematic contamination with DNA.

An exemplary skin test with the peptide antigens for the oncoprotein HPV16-E7 was carried out on patients. Surprisingly, it could be shown that firstly, it is possible to detect a cellular immune reaction against the viral oncoprotein HPV16-E7 in vivo, and secondly, synthetic peptides can replace proteins for skin tests. Thirdly, an association of a positive skin test reaction in the sense of a "delayed type hypersensitivity" with regression of cervical cancer precursors could be observed. Such a correlation has not been previously known. The observation substantiates the potential significance of the antigen HPV16-E7 in a therapeutically effective vaccine and shows the applicability of the skin test according to the invention for determining the immune status with respect to E6 and E7.

For carrying out the example according to the invention, use was made of five relatively long peptides of 30 amino acids each, said peptides overlapping each other, for the oncoprotein HPV16-E7, and a control peptide of random sequence of the same length. The sequence for the 98 amino acids of the HPV16-E7 protein is known (Seedorf et al. J. Gen. Virol., 71, 2719 (1990)). The peptides were produced at the Dep. IHB/AZL (Leiden, Holland) in a "multiple peptide synthesizer". The pepdtides were synthesized with the help of the "Fmoc" technology, precipitated by means of ether from trifluoro acid and subsequently lyophilized. The purity of the peptides was checked by means of "reverse phase high pressure liquidchromatography". Peptides for use with the skin test of the invention can, however, also be produced by any other way which is known to experts.

The sequences stated in a single letter code for the individual peptides tested were:

1. MHGDTPTLHEYMLDLQPETTDLYCYEQLND
2. DLYCYEQLNDSSEEEDEIDGPAGQAEPDRA
3. PAGQAEPDRAHYNIVTFCCKCDSTLRLCVQ
4. CDSTLRLCVQSTHVDIRTLEDLIMGTLGIV
5. STHVDIRTLEDLIMGTLGIVCPICSQKP and as the control peptide:

6. SENKELKKAIDGLQGLLLGLRQRIETLEGK

The single letter code of the amino acids is, for example, explained in Römpps Chemie Lexikon, published by Georg Thieme Verlag, Stuttgart, volume 1, pages 160/161, (1989).

For the skin test, after a sterility test and a pyrogenic test, the peptides were solved in a concentration of 1 mg/ml in 70% glycerin and about 0.01 ml of this solution were injected in a strictly intracutaneous manner into the upper skin and the epidermis of the test person. Each Peptide was used separately (5 HPV16-E7 peptides+1 control peptide). Of course, however, also combinations of the peptides among themselves and/or with respective peptides of HPV E6 can be used. Parallel to the skin test with E7 antigens, in most cases the general defensive condition against classical recall antigens was determined with an immune block, for example Mérieux Multitest "Sero", test system with 7 antigens and a control for determining the status of the cell-mediated immunity, produced by the Serotherapeutisches Institut Wien GmbH under license of Pasteur Merieux S. V., Lyon, France. Reactions with a reddish formation of papules with a diameter of at least 2 mm were evaluated as being positive.

The skin test was carried out on altogether 19 female patients with premalignant or malignant HPV caused lesions. The probability that such diseases are caused by the HPV type 16 is about 50%; in further 40% of the cases, other "high risk" HPV types have to be assumed:

Twelve female patients with relatively severe cervical intra-epithelial formations of neoplasms (ZIN III), 4 of them with a regression indication at the time of the examination (spontaneous regression of Pap III D to Pap II) Seven female patients with cervix carcinomas.

Thus, 19 female patients were tested, 4 of which were regressors, and 15 of which were progressors.

Two men without any indication regarding HPV16 infection served as control persons.

In addition, in a manner commonly known to experts, the skin-tested persons were examined serologically by means of ELISA with "virus like particles (VLPs)" as an antigen with respect to neutralizing antibodies against HPV 16. Serologic examinations are not required for the specific skin test itself, but were carried out in the example as well to increase the scientific meaninfulness of the results. Smear or biopsy material of the lesions was stored for later virus typing by means of PCR at −80° C.; first, examinations were carried out with dot blot (ViraType, Digene Diagnostics, Silver Spring, Md.) with respect to HPV-6/11, -16/18 and -31/33/35. A lymphocyte bank was established for additional in vitro tests.

The female regressors (4/4) showed a slight (in 1 case) to strong (in 3 cases) immune reaction to individual peptides of the oncoprotein E7. The 15 female progressors and the two control persons did not show a clear reactivity in the skin test. Compared to a classical tuberculin reaction, the course of the skin test reaction was clearly delayed. Therefore, the best time for readings was in most cases one week after the testing. Reactions to the control peptide were not found in any case.

The reactions were photodocumented, one reaction was biopsied and examined histologically. Similar to the observations already made in former skin tests with L1, a lymphocytic infiltrate was found, which seemed to be compatible with a "delayed type hypersensitivity reaction". Antibodies against HPV16-L1 were found in 4 of the 7 female patients with a cervix carcinoma and only in one female patient with CIN. In summary, thus the antibody detection against HPV16-L1-VLPs was obviously more associated with a progression, whereas a cellular immune reaction against HPV16-E7 in the skin test was associated with the regression of precancerous cervical lesions.

The results prove the effectiveness of the skin test for a sensitive detection of a cellular immune reaction against HPV16-E7, which, in the cases examined, was associated with a spontaneous regression of an HPV associated cancer precursor lesion.

As, by means of the skin test described, an immune reaction was detected which was associated with regression of cancer precursor lesions, the skin test can be used as an instrument for controlling a vaccination success against E6 and/or E7. A broad screening by means of skin testing for the clarification of the mechanisms of an immunologically mediated tumor regression is also possible. Because of the extremely high expenditure for in vitro experiments, it is hardly possible to test a cellular immunity for a large number of patients by means of laboratory tests. In future studies regarding vaccination with a hypothetically therapeutically effective vaccine against the cervix carcinoma by immunisation against the tumor protein HPV16-E7, the skin test according to the invention is, because it is practicable and sensitive, an ideal method for detecting the desired reaction of the cellular immunological system to the vaccination.

In the example mentioned above, the peptides used were dissolved in 70% glycerin. Glycerin is preferred because it has a viscosity suitable for an intracutaneous application and, in addition, has a disinfecting effect. According to the invention, however, other suitable solvents can also be used; possibly, due to the solubility characteristics of a peptide, it has to be dissolved in a specially adapted solution. Further additives such as emulsifiers, chelating agents, disinfectants and others can also be added to the solvents used according to the invention.

The skin test can be effected by an intracutaneous injection of an effective amount of dissolved E6 and/or E7 antigen by means of a syringe. Accordingly, the diagnosis kit would contain on or more ampoules, syringes and cannulas. According to the invention, the use of applicators specially adapted for skin tests is also possible and preferred, for example the multitest "SERO" test stamp of Sero-Mérieux (see above) or the stamp for the TINE test. Accordingly, the diagnosis kit according to the invention can contain ampoules with antigen(s) and/or applicators.

In the example described above, the way the skin test of the invention works was described with HPV16-E7. However, E6 can be used as well. It is also possible to use the skin test by using E6 and/or E7 of other HPV types for detecting an immunological response with respect to these strains. Because of the close degree of relationship of different HPV types, it is finally also possible to make use of cross-reactions between different HPV types to introduce a more universal skin test against different HPV types at the same time.

The amount of antigens which has to be applied for a visible immune reaction depends on various factors. Accordingly, according to the invention, it can range between 0.01 and 10 μg, preferably between 0.05 and 5 μg antigen per application. In this case, when preparing antigen solutions for diagnosis kits, it has to be taken into account that only part of the solution will get into the intracutaneous region, whereas another part can be lost on the skin of the test person or will remain in the solution ampoule.

What is claimed is:

1. A skin test diagnosis kit for detecting an cellular immune reaction against the oncoprotein E6 and/or E7 of a human papilloma virus type, said diagnosis kit containing an effective amount of the oncoprotein E6 and/or E7 and/or at least an immunologically effective portion of E6 and/or E7 of a human papilloma virus type.

2. The diagnosis kit of claim 1, characterized in that the contained portion of the oncoprotein is derived from HPV16.

3. The diagnosis kit of claim 1, characterized in that the immunologically effective portion of the human papilloma virus type is at least one synthetically produced peptide.

4. The diagnosis kit of claim 1, characterized in that the contained oncoprotein E7 or the immunologically effective portion thereof is or are from HPV16.

5. The diagnosis kit of claim 1, characterized in that the contained oncoprotein or the immunologically effective portion thereof is dissolved in a solvent.

6. The diagnosis kit of claim 5, characterized in that the solvent is 70% glycerin.

7. The diagnosis kit of claim 1, characterized in that the amount of oncoprotein or the immunologically effective portion is 0.01 to 10 µg per charge to be applied.

8. The diagnosis kit of claim 1, characterized in that said diagnosis kit further comprises an applicator, by means of which said effective amount of the oncoprotein or the immunologically effective portion thereof can be injected intracutaneously.

9. The diagnosis kit of claim 8, characterized in that said applicator is a syringe.

10. The diagnosis kit of claim 8, characterized in that said applicator is a test stamp.

11. A process for carrying out a skin test for detecting an immunological response with respect to the oncoproteins E6 and/or E7 of an HPV type, comprising the following steps;
   a) providing a diagnosis kit of claim 1;
   b) intracutaneous application of an effective amount of at least one oncoprotein E6 and E7 or effective portions thereof into a test person;
   c) after a sufficient incubation time, visual inspection of the skin regions of the application to detect an immunological response.

12. The process of claim 11, characterized in that the visual inspection of the skin region takes place one week after application of the oncoprotein.

13. A skin test diagnosis kit for detecting an immune reaction against the oncoprotein E6 and/or E7 of a human papilloma virus type, said diagnosis kit containing an effective amount of the oncoprotein E6 and/or E7 derived from HPV 16 and/or at least an immunologically effective portion of E6 and/or E7 of a human papilloma virus type.

14. A skin test diagnosis kit for detecting an immune reaction against the oncoprotein E6 and/or E7 of a human papilloma virus type, said diagnosis kit containing an effective amount of the oncoprotein E6 and/or E7 and/or at least an immunologically effective portion of E6 and/or E7 of a human papilloma virus type, wherein said immunologically effective portion of the human papilloma virus type is at least one synthetically produced peptide.

15. A skin test diagnosis kit for detecting an immune reaction against the oncoprotein E6 and/or E7 of a human papilloma virus type, said diagnosis kit containing an effective amount of the oncoprotein E6 and/or E7 and/or at least an immunologically effective portion of E6 and/or E7 of a human papilloma virus type, wherein said oncoprotein E7 or the immunologically effective portion thereof is or are from HPV 16.

16. A skin test diagnosis kit for detecting an immune reaction against the oncoprotein E6 and/or E7 of a human papilloma virus type, said diagnosis kit containing an effective amount of the oncoprotein E6 and/or E7 and/or at least an immunologically effective portion of E6 and/or E7 of a human papilloma virus type, wherein said contained oncoprotein or the immunologically effective portion thereof is dissolved in a solvent.

17. The diagnosis kit of claim 16, wherein the solvent is 70% glycerin.

18. A skin test diagnosis kit for detecting an immune reaction against the oncoprotein E6 and/or E7 of a human papilloma virus type, said diagnosis kit containing an effective amount of the oncoprotein E6 and/or E7 and/or at least an immunologically effective portion of E6 and/or E7 of a human papilloma virus type, wherein the amount of oncoprotein or the immunologically effective portion is 0.01 to 10 μg per charge to be applied.

19. A skin test diagnosis kit for detecting an immune reaction against the oncoprotein E6 and/or E7 of a human papilloma virus type, said diagnosis kit containing an effective amount of the oncoprotein E6 and/or E7 and/or at least an immunologically effective portion of E6 and/or E7 of a human papilloma virus type, and further containing an applicator, by means of which said effective amount of the oncoprotein or the immunologically effective portion thereof can be injected intracutaneously. oncoprotein or the immunologically effective portion thereof is dissolved in a solvent.

20. The diagnosis kit of claim 19, wherein said applicator is a syringe.

21. The diagnosis kit of claim 19, wherein said applicator is a test stamp.

22. A process for carrying out a skin test for detecting an immunological response with respect to the oncoproteins E6 and/or E7 of an HPV type, comprising the following steps:
   a) providing skin test diagnosis kit for detecting an immune reaction against the oncoprotein E6 and/or E7 of a human papilloma virus type, said diagnosis kit containing an effective amount of the oncoprotein E6 and/or E7 and/or at least an immunologically effective portion of E6 and/or E7 of a human papilloma virus type;
   b) intracutaneous application of an effective amount of at least one oncoprotein E6 and E7 or effective portions thereof into a test person;
   c) after a sufficient incubation time, visual inspection of the skin regions of the application to detect an immunological response.

23. The process of claim 22, wherein the visual inspection of the skin region takes place one week after application of the oncoprotein.

* * * * *

UNITED STATES PATENT AND TRADEMARK OFFICE
CERTIFICATE OF CORRECTION

PATENT NO.    : 6,478,749 B1
DATED         : November 12, 2002
INVENTOR(S)   : Höpfl It is certified that error appears in the above-identified patent and that said Letters Patent is hereby corrected as shown below:

Title page,
Item [75], Inventor, Innsbruch" should be -- Innsbruck --.

Column 2,
Line 7, "ctherapeutic" should be -- therapeutic --.

Column 3,
Line 1, "pepdtides" should be -- peptides --.
Line 5, "liquidchromatography" should be -- liquid chromatography --.
Line 13, seq. 4, "CDSTLRLCVQSTHVDIRTLEDLIMGTLGIV" should be
-- CDSTLRCVQSTHVDIRTLEDLLMGTLGIV --.
Line 14, seq. 5, "STHVDIRTLEDLIMGTLGIVCPICSQKP" should be
-- STHVDIRTLEDLLMGTLGIVCPICSQKP --. (emphasis added)
Line 43, "ZIN" should be -- CIN --.

Column 7,
Line 38, "an cellular" should be -- a cellular --.

Column 10,
Lines 1-3, "oncoprotein or the Immunologically effective portion thereof is dissolved in a solvent." should be deleted.

Signed and Sealed this

Fourteenth Day of September, 2004

JON W. DUDAS
*Director of the United States Patent and Trademark Office*